United States Patent [19]

Monkovic

[11] 4,115,389

[45] Sep. 19, 1978

[54] PROCESS OF N-DEMETHYLATING (−)-1-(P-METHOXYBENZYL)-2-METHYL-1,2,3,4,5,6,7,8-OCTAHYDROISOQUINOLINE

[75] Inventor: Ivo Monkovic, Candiac, Canada

[73] Assignee: Bristol-Myers Company, New York, N.Y.

[21] Appl. No.: 793,203

[22] Filed: May 2, 1977

[51] Int. Cl.$^2$ ............................................. C07D 217/20
[52] U.S. Cl. ................................. 260/289 D; 260/285
[58] Field of Search ............. 260/283 SY, 289 D, 285

[56] References Cited

U.S. PATENT DOCUMENTS

| | | | |
|---|---|---|---|
| 3,775,414 | 11/1973 | Monkovic et al. | 260/285 |
| 3,819,635 | 6/1974 | Pachter et al. | 260/285 |
| 3,856,795 | 12/1974 | Yardley | 260/283 SY |
| 3,980,641 | 9/1976 | Monkovic et al. | 260/285 X |
| 4,017,497 | 4/1977 | Lim et al. | 260/285 |

OTHER PUBLICATIONS

Ferris et al., J. Org. Chem., vol. 33, pp. 3493–3498 (1968).
Schnieder et al., C.A. 45, pp. 2010d–2011c (1951).
Schnieder et al., C.A. 49, 8975 (1955).
Ferris et al., J. Org. Chem., vol. 33(9), pp. 3493–3498 (1968).
Thyagarajan, Mech. & Mol. Migr., vol. I, Interscience (1968), pp. 176–194.
Smith, The Chem. of Openchain Nitrogen Compounds, vol. II, W. A. Benjamin, N.Y., N.Y. (1966), p. 26 & 27.

*Primary Examiner*—Donald G. Daus
*Assistant Examiner*—D. Springer
*Attorney, Agent, or Firm*—Herbert W. Taylor, Jr.

[57] ABSTRACT

N-Alkyl allylic tertiary amines are dealkylated as illustrated by treatment of (−)-1-(p-methoxybenzyl)-2-methyl-1,2,3,4,5,6,7,8-octahydroisoquinoline in cold methylene chloride with m-chloroperbenzoic acid followed by the addition of aqueous ferrous chloride to provide a good yield of (+)-1-(p-methoxybenzyl)-1,2,3,4,5,6,7,8-octahydroisoquinoline with substantial if not complete retention of optical activity. The product is an intermediate in a synthesis of the analgesic known as butorphanol.

3 Claims, No Drawings

PROCESS OF N-DEMETHYLATING (−)-1-(P-METHOXYBENZYL)-2-METHYL-1,2,3,4,5,6,7,8-OCTAHYDROISOQUINOLINE

BACKGROUND OF THE INVENTION

1. Field of the Invention

This invention relates to a chemical process for dealkylation of N-alkyl allylic tertiary amines as illustrated by the production of (+)-1-(p-methoxybenzyl)-1,2,3,4,5,6,7,8-octahydroisoquinoline from the corresponding N-methyl compound.

2. Description of the Prior Art

The analgesic generically (USAN) named butorphanol and chemically named (−)-17-(cyclobutylmethyl)-morphinan-3,14-diol has been described in U.S. Pat. No. 3,819,635 (and see also U.S. Pat. Nos. 3,775,414, 3,980,641 and 4,017,497).

An alternative synthesis of butorphanol starting with (+)-1-(p-methoxybenzyl)-1,2,3,4,5,6,7,8-octahydroisoquinoline has been disclosed by myself and my colleagues in U.S. application Ser. No. 669,795 filed Mar. 23, 1976. The pertinent disclosure therein is repeated at the end of this specification under the heading "Production of Butorphanol." 1-(p-Methoxybenzyl)-2-methyl-1,2,3,4,5,6,7,8-octahydroisoquinoline is believed to be commercially available and in any event its preparation has been described by Schnider et al., Helv. Chim. Acta, 33, 1437–1448 (1950) and its resolution into optical isomers by Schnider et al., Helv. Chim. Acta, 37, 710-720 (1954) [Chemical Abstracts, 45, 2010 (1951) and 49, 8975 (1955)].

A variety of reactions of amine oxides are reviewed in Mechanisms of Molecular Migrations edited by B. S. Thyagarajan, Volume 1, Interscience Publishers, N.Y., N.Y. 1968 in the section titled "The Polonovski Reaction" on pages 176–194.

Ferris et al., Detoxification Mechanisms. III. The Scope and Mechanism of the Iron-Catalyzed Dealkylation of Tertiary Amine Oxides, J. Org. Chem., 33(9), 3493–3498 (1968) report work as indicated by the title and also review earlier work such as that reported by Craig et al., Tertiary Amine Oxide Rearrangements. III. The Mechanism of the Demethylation of Nicotine, J. Amer. Chem. Soc., 86, 3866–3869(1964).

The Polonovski reaction has also been reviewed on pages 26-27 of Volume II of the Chemistry of Open-Chain Organic Nitrogen Compounds by Peter A. S. Smith, W. A. Benjamin, Inc., N.Y. (1966).

SUMMARY OF THE INVENTION

There is provided by the present invention the process of N-dealkylating an N-alkyl (and especially an N-methyl or N-benzyl) cyclic allylic tertiary amine which comprises the consecutive steps (conducted in one vessel if desired) of reacting each mole of said compound in a chlorinated organic solvent such as methylene chloride, chloroform, carbon tetrachloride, ethylidene chloride and ethylene dichloride or mixtures thereof (or any other organic solvent which is unreactive to peracids) with at least one mole of a peracid such as m-chloroperbenzoic acid, peracetic acid and the like and then reacting the resulting mixture without isolation of the product therein (unless desired) with 0.01 to 1.0 mole, and preferably 0.01 to 0.10 mole and most preferably 0.03 to 0.05 mole, of a ferrous salt which may be water-soluble such as ferrous sulfate and ferrous chloride or may be solvent soluble such as ferrous acetate (in which case the reaction is conducted in the absence of water so that there is only one solvent phase) to produce the corresponding N-dealkylated allylic secondary amine with substantially the same optical purity as that of the starting compound when said starting compound is optically active.

The temperature is not critical; use is usually made of reaction temperatures in the range of −30° to 70° C. and preferably in the range of −20° C. to ambient temperature.

There is further provided by the present invention the process of N-demethylating (−)-1-(p-methoxybenzyl)-2-methyl-1,2,3,4,5,6,7,8-octahydroisoquinoline which comprises the consecutive steps (conducted in one vessel if desired) of reacting each mole of said compound in a chlorinated organic solvent such as methylene chloride, chloroform, carbon tetrachloride, ethylidene chloride and ethylene dichloride or mixtures thereof (or any other organic solvent which is unreactive to peracids) with at least one mole of a peracid such as m-chloroperbenzoic acid, peracetic acid and the like and then reacting the resulting mixture without isolation of the product therein (unless desired) with 0.01 to 1.0 mole, and preferably 0.01 to 0.10 mole and most preferably 0.03 to 0.05 mole, of a ferrous salt which may be water-soluble such as ferrous sulfate and ferrous chloride or may be solvent soluble such as ferrous acetate (in which case the reaction is conducted in the absence of water so that there is only one solvent phase) to produce (+)-1-(p-methoxybenzyl)-1,2,3,4,5,6,7,8-octahydroisoquinoline with substantially the same optical purity as that of the starting compound.

The temperature is not critical; use is usually made of reaction temperatures in the range of −30° to 70° C. and preferably in the range of −20° C. to ambient temperature.

DESCRIPTION OF THE PREFERRED EMBODIMENTS

Example

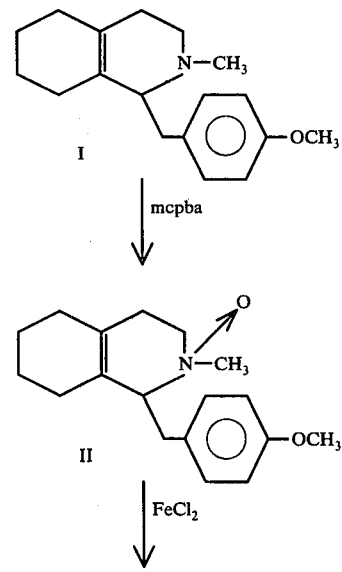

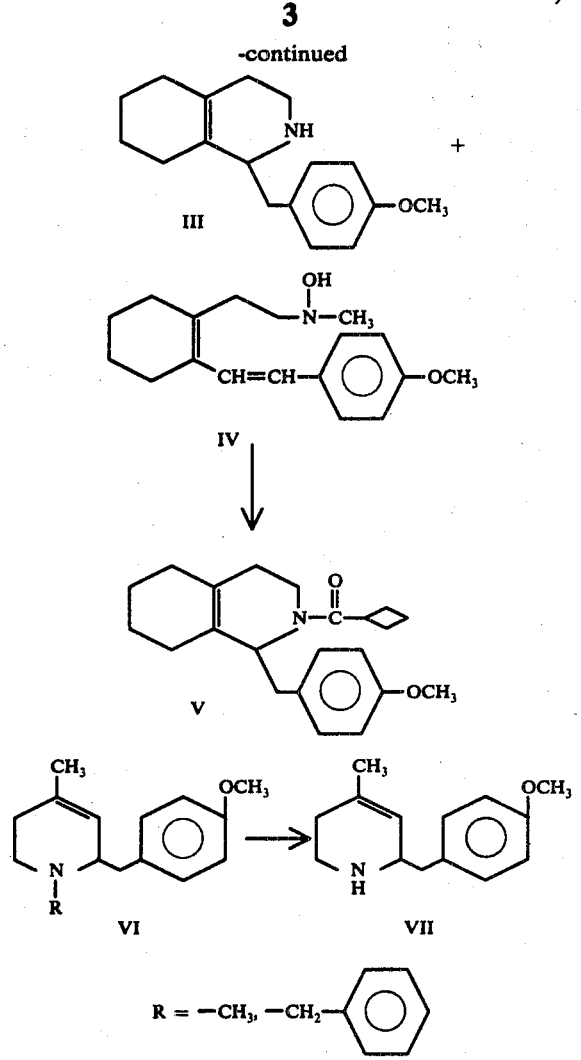

R = —CH₃, —CH₂—⟨phenyl⟩

Demethylation of (−)-1-(p-Methoxybenzyl)-2-methyl-1,2,3,4,5,6,7,8-octahydroisoquinoline (I)

To a cooled (ice-salt) stirred solution of (−) I (2.71 g., 10 m.mol., 74% optical purity) in CH₂Cl₂ (10 ml.) was added in small portions over a period of 10 minutes m-chloroperbenzoic acid (2.0 g., of 85% purity, 10 m.mol.) (mcpba) and stirred for 20 minutes followed by addition of ferrous chloride (0.7 ml. of 1N solution in water). Stirring and cooling continued for 1 hour and then stirring continued for 2 more hours at room temperature. The reaction mixture was worked up as follows. Ethylenediamine (600 mg.), sodium hydroxide (10 ml. of 2N solution) and petroleum ether (20 ml.) were added and after vigorous shaking layers were separated. The aqueous layer was extracted twice with ether-pet. ether mixture (1:3) and combined extracts were dried over K₂CO₃, filtered and the filtrate divided in the two equal parts. The first part was treated with cyclobutanecarboxylic acid chloride (400 mg., 4.44 m.mol.) and triethylamine (500 mg.). The mixture was washed with water, followed by dilute hydrochloric acid and dilute sodium hydroxide respectively. Drying and evaporation of solvent gave 1.1 g. (65%) of V as oil, $[\alpha]_D = -101.5°$ (c 1.03, CHCl₃). The authentic optically pure V has rotation of −145°. Thus the product is 70% optically pure.

The second part was concentrated in vacuo and the residue dissolved in acetone and treated with dry hydrochloric acid solution in ether to give 810 mg. (55%) of (+) III hydrochloride m.p. 187°–188° C., $[\alpha]_D = +117°$ (c 2.08, MeOH). The authentic rotation of III, HCl is +148°. Thus the product is 79% optically pure. Another crop of 70 mg. can be obtained from mother liquors for a total yield of 880 mg. (60%).

Similar yields are obtained by the same procedure in the tetrahydropyridine series: VI→VII.

Production of Butorphanol
CHART I

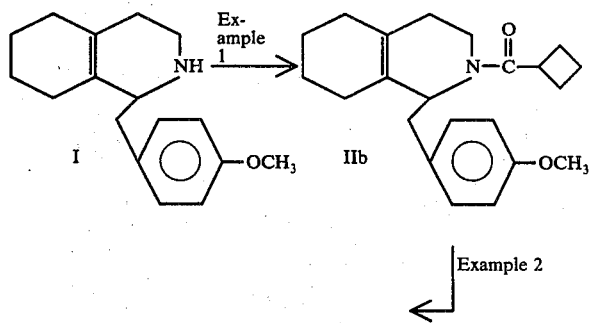

Example 2

Production of Butorphanol
CHART I

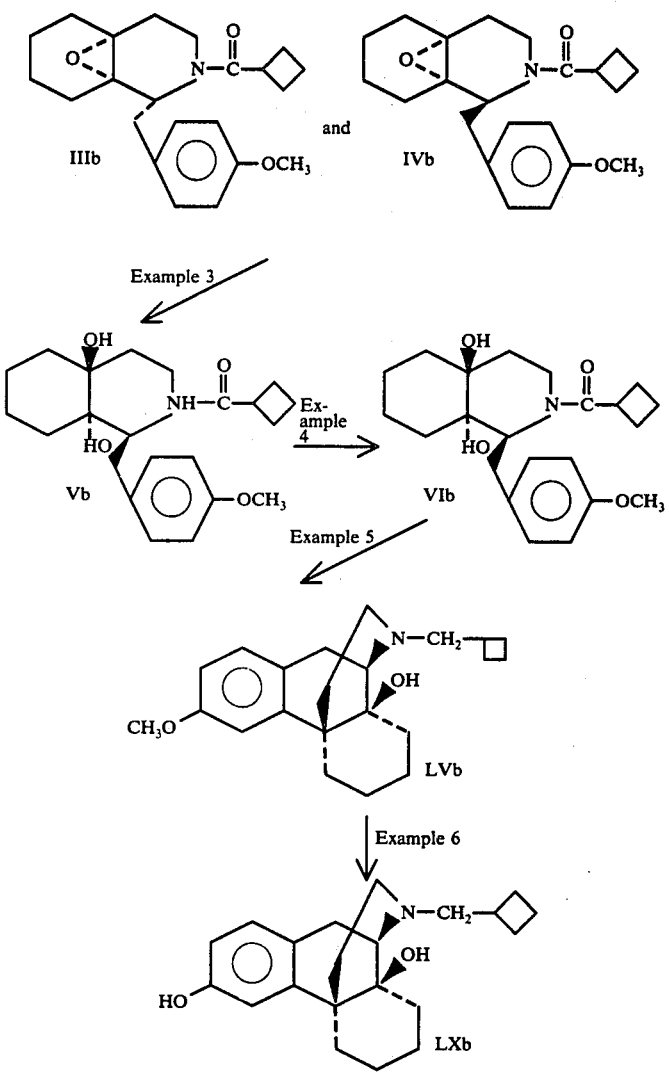

-continued

EXAMPLE 1

(±)-2-Cyclobutylcarbonyl-1-(p-methoxybenzyl)-1,2,3,4,5,6,7,8-octahydroisoquinoline (IIb).

To a stirred and cooled (ice-bath) solution of dl-1-(p-methoxybenzyl)-1,2,3,4,5,6,7,8-octahydroisoquinoline I (9.77 g., 37.7 mmol) and triethylamine (4.04 g., 40 mmol) in dichloromethane (80 ml) was added dropwise a solution of cyclobutylcarbonyl chloride (4.76 g., 40 mmol) in dichloromethane (20 ml). The reaction mixture was then washed with water followed by diluted hydrochloric acid and brine. The organic layer was dried and concentrated in vacuo to give 12.8 of racemic IIb as an oil. Molecular weight calculated for $C_{22}H_{29}NO_2$: 339. Found (mass spectrometry): 339.

The (−)-IIb was obtained in a similar procedure from (+)-Ib; $[\alpha]_D = -145°$ (C, 0.1; CHCl$_3$).

A sample for analysis was distilled at 190-200/0.3 mm.

Anal. calc'd. for $C_{22}H_{29}NO_2$: C, 77.84; H, 8.61; N, 4.13. Found: C, 77.58; H, 8.69; H, 4.38.

EXAMPLE 2

(±)-2-Cyclobutylcarbonyl-9,10-epoxy-1-(p-methoxybenzyl)-perhydroisoquinolines (IIIb and IVb).

To a cooled (ice-bath) stiarred solution of racemic IIb (12.8 g) in dichloromethane (100 ml) was added in several portions m-chloroperbenzoic acid (6.92 g. of 80% purity) and the mixture was left at room temperature for 16 hours. Fifteen ml. of 1M NaHSO$_3$ in water was added to the solution and shaken vigorously. The mixture was then treated with saturated sodium bicarbonate solution with agitation until the evolution of CO$_2$ ceased. The methylene chloride phase was collected, washed with water and dried over anhydrous sodium sulfate. Filtration and evaporation of the methylene chloride gave 13.2 g of a 4:1 mixture of racemic IIIb and IVb as an oil.

Molecular weight calculated for $C_{22}H_{29}NO_3$: 355. Found (mass spectrometry): 355.

A mixture of (+)-IIIb and (+)-IVb, an oil was obtained from (+)-IIb; $[\alpha]_D = +82°$ (C, 0.1; CHCl$_3$).

A sample for analysis was distilled at 200 - 205/0.5 mm.

Anal. calc'd. for $C_{22}H_{29}NO_3$: C, 74.33; H, 8.22; N, 3.94. Found: C, 74.13; H, 8.40; N, 3.76.

A sample of pure IIIb was obtained by column chromatography (silica gel-ether) as white solid; m.p. 109°–110° (from ether); $[\alpha]_D = +70.5$ (C.05, $CHCl_3$).

EXAMPLE 3

($\pm$)-2-Cyclobutylcarbonyl-9$\alpha$,10$\beta$-dihydroxy-1$\beta$-(p-methoxybenzyl)-perhydroisoquinoline (Vb).

To a cooled (ice-bath) solution of a mixture of racemic IIIb and IVb (1.7 g.) in THF [Tetrahydrofuran, 25 ml] was added 15% aqueous perchloric acid (20 ml) and the mixture allowed to stand at room temperature for 16 hours. It was then treated with an ice-cold solution of sodium carbonate (30 ml of 10% solution) and extracted with benzene (2 × 20 ml). The extract was dried and evaporated in vacuo to give an oil, which crystallized from ether. There was obtained 920 mg. of racemic Vb as white solid: m.p. 135°–137°. Recrystallization from ether gave an analytical sample; m.p. 148–150° C.

Anal. calc's. for $C_{21}H_{33}NO_4$: C, 70.75; H, 8.37; N, 3.75. Found: C, 71.12; H, 8.16; N, 3.97.

The optically active Vb was obtained similarly from pure (+)-IIIb as white solid, m.p. 130°–132° from acetonitrile, $[\alpha]_D = -4.0$ (C, 0.4, $CHCl_3$).

EXAMPLE 4

($\pm$)-2-Cyclobutylmethyl-9$\alpha$,10$\beta$-dihydroxy-1$\beta$-(p-methoxybenzyl)-perhydroisoquinoline (VIb).

To a boiling solution of lithium aluminum hydride (300 mg) in THF (8 ml) was added dropwise a solution of 920 mg of racemic Vb in THF (20 ml) and the mixture was heated under reflux for 3 hours. After cooling, the excess lithium aluminum hydride was decomposed by the careful addition of about 0.5 ml of water, followed by filtration and evaporation in vacuo to give 800 mg. of racemic solid VIb; m.p. 120°–122° C.

Molecular weight calculated for $C_{22}H_{33}NO_3$: 359. Found (mass spectrometry): 359.

The optically active VIb was similarly obtained from (−)-Vb; m.p. 136° C., 137° C. from 2-propanol; $[\alpha]_D = -42°$ (C, 0.53; $CHCl_3$).

Anal. Calc'd. for $C_{21}H_{33}NO_3$, C, 73.50; H, 9.25; N 3.90. Found: C, 73.25; H, 9.49; N, 3.90.

EXAMPLE 5

($\pm$)-N-Cyclobutylmethyl-14$\beta$-hydroxy-3-methoxymorphinan (LVb).

To a cooled (ice-bath) solution of VIb (800 mg) in benzene (10 ml) was added 1M borane solution in THF (2.2 ml) and the mixture concentrated in vacuo. To the solid borane complex was added phosphoric acid (16 g., anhydrous) and the mixture was heated at 45° for 16 hours. It was then treated with water (60 ml) and concentrated ammonium hydroxide (24 ml) and extracted with benzene (2 × 20 ml). The benzene extract was dried and concentrated in vacuo to give 600 mg. of crude racemic LVb as an oil. This was dissolved in acetone and treated with dry hydrogen chloride solution in ether to give 500 mg of solid hydrochloride salt of LVb; m.p. 248°–250° C. Reported m.p.: 248°–250° C. The optically active LVb was similarly obtained purified as free base by recrystallization from methanol; m.p. 82°–84° C. $[\alpha]_D = +81.0$ (C, 0.7; MeOH).

If (+)-I is utilized as starting material, then the end product LVb would be levorotatory.

Demethylation of the 3-methoxy group to produce LXb is performed as previously described, e.g. in Example 26 of U.S. Pat. No. 3,819,635.

I claim:

1. The process of N-demethylating (−)-1-(p-methoxybenzyl)-2-methyl-1,2,3,4,5,6,7,8-octahydroisoquinoline which comprises the consecutive steps conducted in one vessel at a temperature in the range of −30° to 50° C. of reacting each mole of said compound in a chlorinated organic solvent selected from the group consisting of methylene chloride, chloroform, carbon tetrachloride, ethylidene chloride and ethylene dichloride with at least one mole of m-chloroperbenzoic acid and then reacting the resulting mixture without isolation of the product therein with 0.01 to 1.0 mole of aqueous ferrous chloride to produce (+)-1-(p-methoxybenzyl)-1,2,3,4,5,6,7,8-octahydroisoquinoline with substantially the same optical purity as that of the starting compound.

2. The process of claim 1 wherein the amount of ferrous chloride is in the range of 0.01 to 0.10 mole.

3. The process of claim 1 wherein the amount of ferrous chloride is in the range of 0.03 to 0.05 mole.

* * * * *